United States Patent [19]

Sievert et al.

[11] Patent Number: 6,147,267

[45] Date of Patent: *Nov. 14, 2000

[54] PROCESS FOR PERFLUOROCYCLOALKANE PURIFICATION

[75] Inventors: Allen Capron Sievert, Elkton, Md.; V. N. Mallikarjuna Rao, Wilmington, Del.

[73] Assignee: E. I. du Pont de Nemours and Company, Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 09/429,272

[22] Filed: Oct. 29, 1999

Related U.S. Application Data

[60] Provisional application No. 60/107,817, Nov. 10, 1998.

[51] Int. Cl.⁷ .................................................... C07C 17/38
[52] U.S. Cl. ............................................................. 570/177
[58] Field of Search ............................................. 570/177

[56] References Cited

U.S. PATENT DOCUMENTS

| | | | |
|---|---|---|---|
| 5,001,287 | 3/1991 | Fernandez et al. | 570/177 |
| 5,105,035 | 4/1992 | Wang et al. | 570/177 |
| 5,569,797 | 10/1996 | Fu et al. | 570/177 |
| 5,780,695 | 7/1998 | Kalnes | 570/177 |
| 5,858,595 | 1/1999 | Merkel et al. | 570/177 |

Primary Examiner—Alan Siegel

[57] ABSTRACT

A process is disclosed for recovering at least one perfluorocycloalkane selected from the group consisting of octafluorocyclobutane, hexafluoro-bis(trifluoromethyl) cyclobutane (1,2 and 1,3; cis and trans), and heptafluoro (trifluoromethyl)cyclobutane from a mixture comprising (a) the perfluorocycloalkane, (b) olefinic impurity and, optionally, (c) saturated chlorine-containing impurity selected from the group consisting of chlorocarbons, hydrochlorocarbons, hydrochlorofluorocarbons, chlorofluorocarbons and mixtures thereof. The process involves (1) contacting the mixture with hydrogen in the presence of a hydrogenation catalyst under conditions suitable for converting at least a portion of the olefinic impurity to a saturated impurity containing at least one fluorine substituent less than the olefin impurity and reducing the chlorine content of at least a portion of the saturated chlorine-containing impurity (if present), and (2) separating said at least one perfluorocycloalkane from the products produced during the hydrogenation of (1).

3 Claims, No Drawings

PROCESS FOR PERFLUOROCYCLOALKANE PURIFICATION

This application claims the priority benefit of U.S. Provisional Application Ser. No. 60/107,817, filed Nov. 10, 1998.

FIELD OF THE INVENTION

The present invention relates to a process for the purification of halofluorocarbons, more particularly, to the purification of perfluorocycloalkanes by the removal of olefinic and/or chlorine-containing fluorocarbons.

BACKGROUND OF THE INVENTION

Perfluorocyclobutane (C-318, b.p. −6° C.) is a valuable material which can be used as a propellant, etch gas and fire extinguishant. This compound is typically made by cyclodimerization of tetrafluoroethene (TFE) or is recovered as a by-product from the manufacture of TFE. As a result C-318 may be contaminated with unsaturates such as E- and Z-perfluoro-2-butene (i.e., $CF_3CF\!=\!CFCF_3$ or FC-1318my) and perfluoroisobutene (i.e., $(CF_3)_2C\!=\!CF_2$ or PFIB or FC-1318mmt). These compounds, especially the latter, are highly toxic and must be removed prior to commercial use. FC-1318's are difficult to separate from C-318 by distillation as the boiling points are similar.

U.S. Pat. No. 5,001,287 discloses a process for treating an impure mixture consisting essentially of at least one olefinic impurity and at least one saturated halocarbon by contacting the mixture with a source of hydrogen in the presence of a hydrogenation catalyst. The saturated halocarbon includes perfluorocyclobutane and the catalyst includes Group VIII metals and rhenium. The olefinic impurity is converted to a hydrogenated form. For example, $CF_3CH_2F$ containing $CF_2\!=\!CHCl$ impurity may be treated to produce $CF_3CH_2F$ containing $CHF_2CH_2Cl$.

There is a need for alternative methods of purification. In particular, in the case of purifying certain perfluorocycloalkanes, there is a need for a process for obtaining products of reaction of the olefinic impurity which are not simply products of adding hydrogen at the point of unsaturation.

SUMMARY OF THE INVENTION

This invention provides a process for recovering at least one perfluorocycloalkane selected from the group consisting of octafluorocyclobutane, hexafluorobis(trifluoromethyl) cyclobutane (1,2 and 1,3; cis and trans), and heptafluoro (trifluoromethyl)cyclobutane from a mixture comprising (a) said at least one perfluorocycloalkane and (b) olefinic impurity (i.e., one or more olefinic compounds) containing fluorine. The process comprises (1) contacting the mixture with hydrogen in the presence of a hydrogenation catalyst selected from the group consisting of platinum and iridium under conditions suitable for converting at least a portion of the olefinic impurity to a saturated impurity containing at least one fluorine substituent less than the olefinic impurity, and (2) separating said at least one perfluorocycloalkane from the products produced during the hydrogenation in (1).

DETAILS OF THE INVENTION

The process of the invention is conducted by contacting either batchwise, or continuously, an impure mixture comprising at least one olefinic impurity and at least one perfluorocycloalkane selected from the group consisting of octafluorocyclobutane, hexafluorobis(trifluoromethyl) cyclobutane (1,2 and 1,3; cis and trans), and heptafluoro (trifluoromethyl)cyclobutane, with hydrogen in the presence of a hydrogenation catalyst.

The perfluorocycloalkanes recovered in accordance with this invention are known compounds in the art. For example, octafluorocyclobutane is typically produced during the manufacture of tetrafluoroethene and hexafluoropropene by the pyrolysis of chlorodifluoromethane as discussed in U.S. Pat. No. 5,672,784.

Representative olefins which can be removed from perfluorocycloalkanes by the process of this invention include, but are not limited to, $CF_2\!=\!CF_2$, $CClF\!=\!CF_2$, $CF_3CF\!=\!CF_2$, $CClF_2CF\!=\!CF_2$, cyclo-$C_4F_6$, cyclo-$C_5F_8$, $CF_3CF\!=\!CFCF_3$, $CF_3CCl\!=\!CHCF_3$, $CF_3CCl\!=\!CClCF_3$, $(CF_3)_2C\!=\!CF_2$ and $CF_2\!=\!CFCF_2CF_3$. The hydrogen treatment can also remove other unsaturates such as $CF_3C\!\equiv\!CCF_3$ (perfluoro-2-butyne).

The mixture which is contacted with hydrogen may also contain a saturated chlorine-containing impurity selected from the group consisting of chlorocarbons, hydrochlorocarbons, hydrochlorofluorocarbons, chlorofluorocarbons, and mixtures thereof. The hydrogen contact may be run under conditions suitable for reducing the chlorine content of at least a portion of these compounds (e.g., by forming hydrocarbons and/or hydrofluorocarbons by hydrodechlorination). The chlorine-depleted saturated impurity produced by this hydrogen contact can also be separated from the perfluorocycloalkane(s). Representative saturated impurities which can be removed from perfluorocycloalkanes by the process of this invention include, but are not limited to, $CHClF_2$, $CCl_2F_2$, $CHClFCF_3$, $CHF_2CClF_2$, $CClF_2CClF_2$, $CCl_2FCF_3$, and $CClF_2CF_3$. The hydrogenation catalysts suitable for the process of this invention comprise metals selected from the group consisting of platinum and iridium or mixtures thereof. Mixtures of platinum and palladium, iridium and palladium, platinum and rhenium, iridium and rhenium may also be used to advantage.

The metal catalysts are preferably supported on carbon. The concentration of metal supported on carbon is typically within the range of about 0.1% to about 10% by weight based on metal and the support.

The carbon support includes activated carbon and acid-washed carbons (e.g., carbons which have been treated with hydrochloric acid or hydrochloric acid followed by hydrofluoric acid). Suitable acid treatment of carbons is described in U.S. Pat. No. 5,136,113. Wood-based carbons, such as coconut shell based carbon, are preferred for the acid treatment.

The carbon catalyst also includes three dimensional matrix porous carbonaceous materials. Examples are those described in U.S. Pat. No. 4,978,649. Of note are three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

The hydrogenation of the olefinic impurities and chlorine-containing saturated impurities over the aforementioned catalysts may be carried out at a temperature of from about 100° C. to about 500° C., preferably from about 150° C. to about 450° C., and most preferably from about 200° C. to about 400° C. If it is desired to remove chlorine-containing saturated impurities, then higher temperatures (about 350° C. to about 450° C.) are preferred. At temperatures of 350° C. and higher some cleavage of the carbon-carbon bonds of the products of hydrogenation of the olefinic and saturated impurities occurs with the result that low boiling impurities such as ethane or 1,1,1-trifluoroethane (HFC-143a) are formed.

The pressure used in the hydrogenation is not critical and may be subatmospheric, atmospheric, or superatmospheric. Preferably, the hydrogenation is done at atmospheric pressure or, for convenience in separations later in the process, at pressures up to 30 atmospheres.

Contact time over the catalyst may vary from about 1 second to about 200 seconds depending on the type of impurities (olefins versus saturated compounds); a contact time of about 5 seconds to about 60 seconds is generally preferred. Longer contact times are preferred if it is desired to convert all saturated compounds containing chlorine to hydrogenated compounds.

The molar ratio of hydrogen to the impurity(ies) should be from about 1:1 to about 500:1, preferably from about 10:1 to about 100:1. Large excesses of hydrogen may cause difficulty in isolation of the perfluorocyclobutane or hydrogenated products.

The hydrogenation of a fluoroolefin typically causes addition of $H_2$ across the carbon-carbon double bond of the fluoroolefin to give a saturated hydrofluorocarbon having the same number of fluorine substituents as in the starting olefin. The resulting saturated hydrofluorocarbon product often has a higher boiling point than either or both of the starting olefin or the perfluorocycloalkane. This wider separation in boiling points of the impurity(ies) versus the desired perfluorocycloalkane enables easier separation of the impurity (ies) by distillation.

For example, olefinic impurities often present in perfluorocyclobutane (C-318) include $CF_3CF=CFCF_3$ (FC-1318my) and $(CF_3)_2C=CF_2$ (FC-1318mmt or PFIB). The boiling points of these compounds are, C-318, −6.1° C.; FC-1318my, 0° C.; and PFIB, 7° C. The hydrogenated olefin products are $CF_3CHFCHFCF_3$ (HFC-338mee) and $(CF_3)_2CHCHF_2$ (HFC-338pz) with boiling points of about 33° C. (mixed isomers) and 17° C., respectively.

Other unsaturated impurities that may be present in C-318 are $CF_3CF=CF_2$ (HFP), $CClF_2CF=CF_2$ (CFC-1215yc), $CF_2=CFCF_2CF_3$ (FC-1318yc) and $CF_3C\equiv CCF_3$. The boiling points of these compounds are −29.4° C., 7.3° C., 4.8° C., and −24.6° C., respectively. The hydrogenated products from these unsaturated impurities are $CF_3CHFCHF_2$ (HFC-236ea), $CClF_2CHFCHF_2$ (HCFC-235eb), $CHF_2CHFCF_2CF_3$ (HFC-338pe) and $CF_3CH_2CH_2CF_3$ (HFC-356mff) with boiling points of ca. 4–6° C., ca. 30–40° C., 34.5° C., and 24.6° C., respectively.

Surprisingly, we have found that use of the preferred hydrogenation catalysts in the process of the invention can result in loss of at least one fluorine substituent from the hydrofluorocarbon which results from addition of hydrogen to the olefin impurity. Also, use of the preferred hydrogenation catalysts in the process of the invention can result in loss of at least one fluorine substituent from a hydrofluorocarbon which results from hydrodechlorination of the chlorine-containing saturated impurity. These hydrodefluorinated products often have boiling points that are even further removed from the boiling point of the perfluorocycloalkane.

For example, hydrogenation followed by hydrodefluorination of the olefinic impurities FC-1318my and PFIB would give the compounds $CF_3CHFCH_2CF_3$ (HFC-347mef) or HFC-356mff and $(CF_3)_2CHCH_3$ (HFC-356mmz) with boiling points of ca. 30° C., 24.6° C. and 21.5° C., respectively.

Similarly, hydrogenation followed by hydrodefluorination of the olefinic impurities $CF_3CF=CF_2$ (HFP), $CClF_2CF=CF_2$ (CFC-1215yc), and $CF_2=CFCF_2CF_3$ (FC-1318yc) would give $CF_3CH_2CHF_2$ (HFC-245fa), $CF_3CHFCH_2F$ (HFC-245eb), $CHF_2CHFCHF_2$ (HFC-245ea) and $CHF_2CH_2CF_2CF_3$ (HFC-338pf) with boiling points of 18° C., 21° C., 40° C. and 33° C., respectively.

Hydrodechlorination of the chlorine-containing saturated impurities $CHClF_2$, $CCl_2F_2$, $CHClFCF_3$, $CHF_2CClF_2$, $CCl_2FCF_3$, $CClF_2CClF_2$, and $CClF_2CF_3$ having boiling points of −40.8° C., −29.8° C., −12° C., −10.2° C., 3.0° C., 3.6° C., and −38.7° C., respectively, gives $CH_2F_2$, $CHClF_2$, $CH_2FCF_3$, $CHF_2CHF_2$, $CHClFCF_3$, $CHF_2CClF_2$, and $CHF_2CF_3$ having boiling points of −51.7° C., −40.8° C., −26.5° C., −19.7° C., −12° C., −10.2° C., and −48.5° C., respectively. Further hydrodefluorination of $CH_2F_2$ and $CH_2FCF_3$ would give $CH_3F$ (HFC-41) and $CH_3CF_3$ (HFC-143a) boiling at −78.5° C. and −47.6° C., respectively.

To the extent that carbon-carbon bond cleavage occurs, lower molecular weight compounds, such as ethane, are formed which typically have low boiling points and are thus easily separated from the desired perfluorocycloalkanes by distillation.

Without further elaboration, it is believed that one skilled in the art can, using the description herein, utilize the present invention to its fullest extent. The following embodiments are to be construed as illustrative, and not as constraining the remainder of the disclosure in any way whatsoever.

EXAMPLES

| Legend | |
|---|---|
| 124 is $CF_3CHClF$ | 143a is $CH_3CF_3$ |
| E/Z-1318my is cis- and trans-$CF_3CF=CFCF_3$ | |
| 1318 isomer is $C_4F_8$ | 254 is $C_3H_4F_4$ |
| C-318 is perfluorocyclobutane | 329 is $C_4HF_9$ |
| 338mee is $CF_3CHFCHFCF_3$ | 347 is $C_3H_4F_4$ |
| AWC is acid-washed carbon | |

Hydrogenation of C-318 Contaminated with FC-1318's

The hydrogenation reactor consisted of a 5 inch (12.7 cm)×0.5 inch (1.3 cm) o.d. section of Hastelloy™ C nickel alloy tubing. For Comparative Example A, the reactor was packed with 0.5% Pd on carbon (10 mL, 3.82 g); the catalyst was held in place by an Inconel™ nickel alloy screen. The reactor, oriented vertically, was placed in a fluidized sand bath at 100° C. and purged with 20 sccm ($3.3 \times 10^{-7}$ m³/s) of a 1:1 $N_2$:$H_2$ mixture while the bath temperature was increased to 250° C. The $N_2$ flow was then shut down and the reactor purged with $H_2$ at 20 sccm ($3.3 \times 10^{-7}$ m³/s) at 250° C. for one hour. Mixtures of C-318 and $H_2$ were fed to the reactor at 200–350° C.; the results are summarized in Table A. An analysis of the starting material is given in Table 1.

For Example 1, the reactor was packed with 1% Pt on acid-washed carbon (AWC, 10 mL, 4.95 g). The reactor was placed in a fluidized sand bath at 100° C. and purged with 20 sccm ($3.3 \times 10^{-7}$ m³/s) of a 1:1 $N_2$:$H_2$ mixture while the bath temperature was increased to 250° C. and then held at 250° C. for one hour. Mixtures of C-318 and $H_2$ were fed to the reactor at 200–350° C.; the results are summarized in Table 2.

For Example 2, the reactor was packed with 2% Ir on acid-washed carbon (AWC, 10 mL, 3.96 g); this catalyst had been previously treated with hydrogen at 900° C. The reactor was placed in a fluidized sand bath at 100° C. and run through the drying cycle as above. Mixtures of C-318 and $H_2$ were fed to the reactor at 200–350° C.; the results are summarized in Table 3.

GC analyses of portions of the reactor vapor effluent were carried out on a 20 foot (6.1 m)×0.125 inch (3.2 mm) steel column packed with 5% Krytox™ 143AC perfluoroether on 60/80 mesh (0.25/0.18 mm) Carbopak BHT. The temperature program was 60° C. initially for 4 minutes, then 8° C./minute ramp to 190° C.

GC-MS analyses were run on a 105 m×0.25 mm id Rtx-1 column (1.0 micron film thickness). The temperature program was −20° C. for 10 minutes, ramp at 10° C./minute to 150° C., and hold for 30 minutes; the helium flow rate through the column was 1.2 mL/min.

TABLE 1

Composition of C-318 Sample Used for Hydrogenation Studies

| Component | GC Area % |
|---|---|
| C-318 | 95.25 |
| 124 | 0.06 |
| E/Z-1318my | 4.45 |
| 1318 isomer | 0.02 |
| 329 | 0.20 |
| Others | 0.02 |

TABLE A (Comparative Example A)
Reaction of the C-318 Mixture with Hydrogen over 0.5% Pd on Carbon

| Temp. | Flow Rates, cc/min | | GC Area Percent | | | | |
|---|---|---|---|---|---|---|---|
| ° C. | $H_2$ | C-318 | C-318 | 329 | 338mee | 347 | 254 |
| 198 | 10 | 10 | 93.8 | 0.13 | 6.0 | 0 | 0 |
| 200 | 20 | 10 | 93.7 | 0.13 | 6.2 | 0 | 0 |

TABLE A-continued (Comparative Example A)
Reaction of the C-318 Mixture with Hydrogen over 0.5% Pd on Carbon

| Temp. | Flow Rates, cc/min | | GC Area Percent | | | | |
|---|---|---|---|---|---|---|---|
| ° C. | $H_2$ | C-318 | C-318 | 329 | 338mee | 347 | 254 |
| 250 | 20 | 10 | 93.3 | 0.16 | 6.5 | 0 | 0 |
| 250 | 10 | 10 | 93.8 | 0.13 | 6.0 | 0 | 0 |
| 200 | 10 | 10 | 93.5 | 0.16 | 6.4 | 0 | 0 |
| 150 | 10 | 10 | 93.7 | 0.16 | 6.2 | 0 | 0 |
| 301 | 10 | 10 | 95.5 | 0.10 | 4.4 | 0 | 0 |
| 350 | 10 | 10 | 95.1 | 0.14 | 3.7 | 1.0 | 0.03 |
| 350 | 20 | 10 | 94.6 | 0.15 | 4.2 | 1.0 | 0.04 |
| 300 | 20 | 10 | 94.2 | 0.14 | 5.6 | 0 | 0 |
| 250 | 5 | 10 | 95.6 | 0.11 | 4.3 | 0 | 0 |

TABLE 2

(Example 1)
Reaction of the C-318 Mixture with Hydrogen over 1% Pt on AWC

| Temp. | Flow Rates, cc/min | | GC Area Percent | | | | | |
|---|---|---|---|---|---|---|---|---|
| ° C. | $H_2$ | C-318 | C-318 | 329 | 338mee | 347 | 254 | $C_2H_6$ |
| 200 | 20 | 10 | 93.6 | 0.18 | 4.5 | 1.7 | 0 | 0 |
| 249 | 20 | 10 | 94.1 | 0.13 | 4.4 | 1.3 | 0 | 0 |
| 250 | 10 | 10 | 94.4 | 0.17 | 3.8 | 1.7 | 0 | 0 |
| 301 | 10 | 10 | 94.2 | 0.17 | 3.3 | 2.3 | 0 | 0 |
| 303 | 20 | 10 | 93.1 | 0.21 | 4.1 | 2.5 | 0 | 0 |
| 350 | 20 | 10 | 91.8 | 0.14 | 0.94 | 6.2 | 0.33 | 0.08 |

TABLE 3

(Example 1)
Reaction of the C-318 Mixture with Hydrogen Over 2% Ir on AWC

| Temp. | Flow Rates, cc/min | | GC Area Percent | | | | | | |
|---|---|---|---|---|---|---|---|---|---|
| ° C. | $H_2$ | C-318 | C-318 | 329 | 338mee | 347 | 254 | $C_2H_6$ | 143a |
| 200 | 10 | 10 | 93.9 | 0.19 | 0.53 | 5.4 | 0 | 0 | 0 |
| 201 | 20 | 10 | 92.7 | 0.24 | 0.44 | 6.6 | 0 | 0 | 0 |
| 250 | 10 | 10 | 93.7 | 0.22 | 0.93 | 5.1 | 0 | 0 | 0 |
| 250 | 20 | 10 | 92.5 | 0.27 | 1.3 | 5.9 | 0 | 0 | 0 |
| 301 | 10 | 10 | 93.3 | 0.25 | 1.2 | 5.2 | 0.01 | 0.05 | 0.02 |
| 300 | 20 | 10 | 92.0 | 0.30 | 1.3 | 6.3 | 0 | 0.05 | 0 |
| 350 | 10 | 10 | 90.7 | 0.18 | 0.31 | 3.6 | 0.03 | 5.0 | 0.15 |
| 349 | 20 | 10 | 89.1 | 0.27 | 0.91 | 5.3 | 0 | 4.1 | 0.20 |

In all the examples only low levels (<0.005 area %) of FC-1318 isomers were observed in equilibrated reactor effluent.

Example 3

Preparation of 1% Platinum on Acid-washed Carbon

A sample of Engelhard carbon (6×16 mesh) was soaked in 1M aqueous HCl and washed with deionized water until chloride-free when tested with silver ntirate (see U.S. Pat. No. 5,136,113). The acid-washed carbon was dried and collected on a 16 mesh screen to remove dust.

A 50 g sample of the acid-washed carbon was added to an aqueous solution of hexachloroplatinic acid containing about 0.5 g of platinum. The slurry stood for one hour at room temperature with occasional stirring. The catalyst was then dried at 120° C. over the course of eighteen hours in the presence of air.

A sample of the dried catalyst was then placed in a quartz boat and heated under a flow of helium to 150° C. for one hour. The catalyst was then treated with 200 sccm ($3.3 \times 10^{-6}$ m$^3$/s) of a 1:1 mixture of helium:hydrogen at 150° C. for one hour. The temperature was then increased to 300° C. and held for eight hours. Hydrogen flow was terminated and the catalyst was allowed to cool in a flow of helium. The catalyst was passivated in a flow of 1.5% oxygen in nitrogen at room temperature.

Example 4

Preparation of 2% Iridium on Acid-washed Carbon

Following a procedure similar to that above, 54 g of acid-washed Calsicat carbon was added to a solution of IrCl$_3$ in aqueous hydrochloric acid containing about 1 g of iridium. The slurry was allowed to stand for about three hours at room temperature with frequent stirring and then dried at 120° C. for eighteen hours in the presence of air. Prior to use, the catalyst was heated for 16 hours in a stream of 20 sccm ($3.3 \times 10^{-7}$ m$^3$/s) hydrogen at a 900° C.

What is claimed is:

1. A process for recovering at least one perfluorocycloalkane selected from the group consisting of octafluorocyclobutane, 1,2-hexafluorobis(trifluoromethyl) cyclobutane, 1,3-hexafluorobis(trifluoromethyl) cyclobutane, and heptafluoro(trifluoromethyl)cyclobutane from a mixture comprising (a) said at least one perfluorocycloalkane and (b) olefinic impurity containing fluorine, comprising:

(1) contacting the mixture with hydrogen in the presence of a hydrogenation catalyst selected from the group consisting of platinum and iridium, under conditions suitable for converting at least a portion of the olefinic impurity to a saturated impurity containing at least one less fluorine substituent than the olefin impurity; and (2) separating said at least one perfluorocycloalkane from the saturated impurity produced from the olefinic impurity in (1).

2. The process of claim 1 wherein the mixture further comprises saturated chlorine-containing impurity selected from the group consisting of chlorocarbons, hydrochlorocarbons, hydrochlorofluorocarbons and chlorofluorocarbons; and wherein the mixture is contacted with hydrogen under conditions suitable for reducing the chlorine content of at least a portion of said chlorine-containing impurity.

3. The process of claim 1 wherein perfluorocyclobutane is recovered from a mixture comprising perfluorocyclobutane and CF$_3$CF=CFCF$_3$; and wherein the contact with hydrogen results in formation of CF$_3$CHFCH$_2$CF$_3$.

* * * * *